(12) United States Patent
Radwanski et al.

(10) Patent No.: US 9,901,668 B2
(45) Date of Patent: Feb. 27, 2018

(54) INDICATING TO A MEDICAL DEVICE PERFORMANCE OF AN OPERATION BY ANOTHER MEDICAL DEVICE

(71) Applicant: Fenwal, Inc., Lake Zurich, IL (US)

(72) Inventors: Katherine Radwanski, Des Plaines, IL (US); William H. Cork, Mettawa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 197 days.

(21) Appl. No.: 14/659,743

(22) Filed: Mar. 17, 2015

(65) Prior Publication Data

US 2016/0271313 A1 Sep. 22, 2016

(51) Int. Cl.
*A61M 1/34* (2006.01)
*G06F 19/00* (2018.01)

(52) U.S. Cl.
CPC ............. *A61M 1/34* (2013.01); *G06F 19/366* (2013.01); *A61M 2205/50* (2013.01); *A61M 2205/60* (2013.01)

(58) Field of Classification Search
CPC combination set(s) only.
See application file for complete search history.

(56) References Cited

U.S. PATENT DOCUMENTS

| 5,885,245 | A | 3/1999 | Lynch et al. |
| 6,626,355 | B2 | 9/2003 | Sasse et al. |
| 6,695,806 | B2 | 2/2004 | Gelfand et al. |
| 7,072,769 | B2 | 7/2006 | Fletcher-Haynes et al. |
| 7,422,693 | B2 | 9/2008 | Carter et al. |
| 7,430,478 | B2 | 9/2008 | Fletcher-Haynes et al. |
| 7,465,285 | B2 | 12/2008 | Hutchinson et al. |
| 7,490,766 | B2 | 2/2009 | Auchinleck |
| 7,661,582 | B2 | 2/2010 | Mollstam |
| 8,204,694 | B2 | 6/2012 | Hauck et al. |
| 8,257,299 | B2 | 9/2012 | Childers et al. |
| 8,267,308 | B2 | 9/2012 | Devergne et al. |
| 8,287,818 | B2 | 10/2012 | Kantrowitz et al. |

(Continued)

FOREIGN PATENT DOCUMENTS

| EP | 1170023 A2 | 1/2002 |
| WO | 2012120078 A2 | 9/2012 |

(Continued)

OTHER PUBLICATIONS

ADASorb Therapeutic Apheresis, brochure, http://tiny.cc/bsanvx, printed from the Internet Mar. 17, 2015, 5 pages.

(Continued)

*Primary Examiner* — Dirk Bass
(74) *Attorney, Agent, or Firm* — Becker Patent Law, LLC

(57) ABSTRACT

A medical device includes a mechanism configured to perform a first medical operation, a scanner and a processing circuit. The scanner is configured to scan data displayed on a computer screen by a second medical device separate from the medical device. The processing circuit is configured to receive the scanned data from the scanner. The scanned data comprises an indication that a second medical operation was performed by the second medical device. The processing circuit is configured to proceed with the first medical operation based on the indication that the second medical operation was performed by the second medical device.

20 Claims, 3 Drawing Sheets

(56) References Cited

U.S. PATENT DOCUMENTS

| | | |
|---|---|---|
| 8,400,298 B2 | 3/2013 | Rada |
| 8,459,543 B2 | 6/2013 | Devergne et al. |
| 8,612,257 B2 | 12/2013 | Zaitsu et al. |
| 8,746,547 B2 | 6/2014 | Mollstam et al. |
| 9,081,001 B2 | 7/2015 | Cook et al. |
| 9,238,097 B2 | 1/2016 | Briggs |
| 2002/0013551 A1 | 1/2002 | Zaitsu et al. |
| 2005/0020961 A1 | 1/2005 | Burbank et al. |
| 2005/0049539 A1 | 3/2005 | O'Hara, Jr. et al. |
| 2007/0191787 A1* | 8/2007 | Lim ................. A61B 5/411 604/246 |
| 2010/0282834 A1 | 11/2010 | Devergne et al. |
| 2012/0212455 A1 | 8/2012 | Kloeffel |
| 2013/0197419 A1 | 8/2013 | Min et al. |
| 2014/0045668 A1 | 2/2014 | Case et al. |
| 2014/0057771 A1 | 2/2014 | Case et al. |

FOREIGN PATENT DOCUMENTS

| | | |
|---|---|---|
| WO | 2014123521 A1 | 8/2014 |
| WO | WO2014210055 | 12/2014 |

OTHER PUBLICATIONS

"New Macogenic G2 for Extracorporeal Photochemotherapy," printed from the Internet Mar. 17, 2015, http://www.macopharma.com/en/category/biotherapy/photopheresis/.

"Xuri Cell Expansion System," printed from the Internet Mar. 17, 2015, https://promo.gelifesciences.com/GL/XURI/expansion.html.

"Fresenius Kabi Introduces Lovo Cell Processing System," printed from the Internet Mar. 17, 2015, https://www.fenwalinc.com/PressReleases/Pages/News/Fresenius-Kabi-Introduces-Lovo-Cell-Processing.aspx.

US 8,424,754, 04/2013, Devergne et al. (withdrawn)

European Search Report, Application No. 16159693.7, dated Sep. 14, 2017, 8 pages.

\* cited by examiner

INDICATING TO A MEDICAL DEVICE PERFORMANCE OF AN OPERATION BY ANOTHER MEDICAL DEVICE

BACKGROUND

The present application relates generally to indicating to a medical device the performance of an operation by another medical device.

Whole blood is made up of various cellular and non-cellular components such as red cells, white cells and platelets suspended in its liquid component, plasma. Whole blood can be separated into its constituent components (cellular, liquid or other) using apheresis, and the separated component can be administered to a patient in need of that particular component.

The administration of blood and/or blood components is common in the treatment of patients suffering from disease. Infusion of white blood cells (i.e., mononuclear cells or MNCs), after the cells have undergone some additional processing or treatment, may also be prescribed for therapeutic reasons including treatment of diseases that specifically involve the white blood cells. Thus, it is often desirable to separate and collect the desired blood component from whole blood and then treat the patient with the specific blood component. The remaining components may be returned to the donor or retained for other uses.

Extracorporeal photopheresis (also sometimes referred to as extracorporeal photochemotherapy) may be a process that includes: (1) collection of MNCs from a patient, (2) photoactivation treatment of the collected MNC cells; and (3) reinfusion of the treated cells back to the patient. More specifically, ECP may involve the extracorporeal exposure of peripheral blood mononuclear cells combined with a photoactive compound, such as 8-methoxypsoralen or "8-MOP" which is then photoactivated by ultraviolet light, followed by the reinfusion of the treated mononuclear cells to the patient. It is believed that the combination of 8-MOP and UV radiation causes apoptosis or programmed cell death of ECP-treated T-cells.

Photopheresis methods include online and offline methods. In online methods, a dedicated photopheresis device may be used to perform the therapy and reinfusion of treated MNCs. Such devices are "dedicated" photopheresis devices, designed only for performing photopheresis and do not perform other collection protocols needed in a hospital or blood processing setting including, for example, multifunctional apheresis protocols for collection of platelets, plasma, RBCs, granulocytes and/or perform plasma/RBC exchange protocols. In offline photopheresis methods, a multifunctional apheresis device may be used to collect mononuclear cells. The collected MNCs, typically contained in one or more collection containers, are severed or otherwise separated from the tubing set used during collection, where they are later treated in a separate irradiation or UVA light device followed by manual reinfusion of the treated cells to a patient. However, during such offline methods, when the cells are transferred from the apheresis device to the irradiation device (which device may be located in another room or laboratory) communication with the donor must be severed and accordingly, the cells detached from the donor. Thus, additional traceability procedures are required to insure that the treated MNC product is ultimately reinfused into the correct donor. In offline photopheresis systems, cell irradiation is documented using paperwork and is only linked back to the apheresis collection through paper records.

DETAILED DESCRIPTION OF ILLUSTRATIVE EMBODIMENTS

One or more embodiments described herein may help ensure that a step in a medical process or procedure is performed before continuing the process or procedure.

One or more embodiments may electronically link an apheresis collection and an irradiation step to act as a measure to ensure that irradiation was successfully completed.

One or more embodiments help avoid potential errors in documentation and the possibility that cells are reinfused to a patient without being irradiated properly (insufficient or no irradiation).

One or more embodiments may allow two devices manufactured by different companies to communicate with one another.

Figure 1:
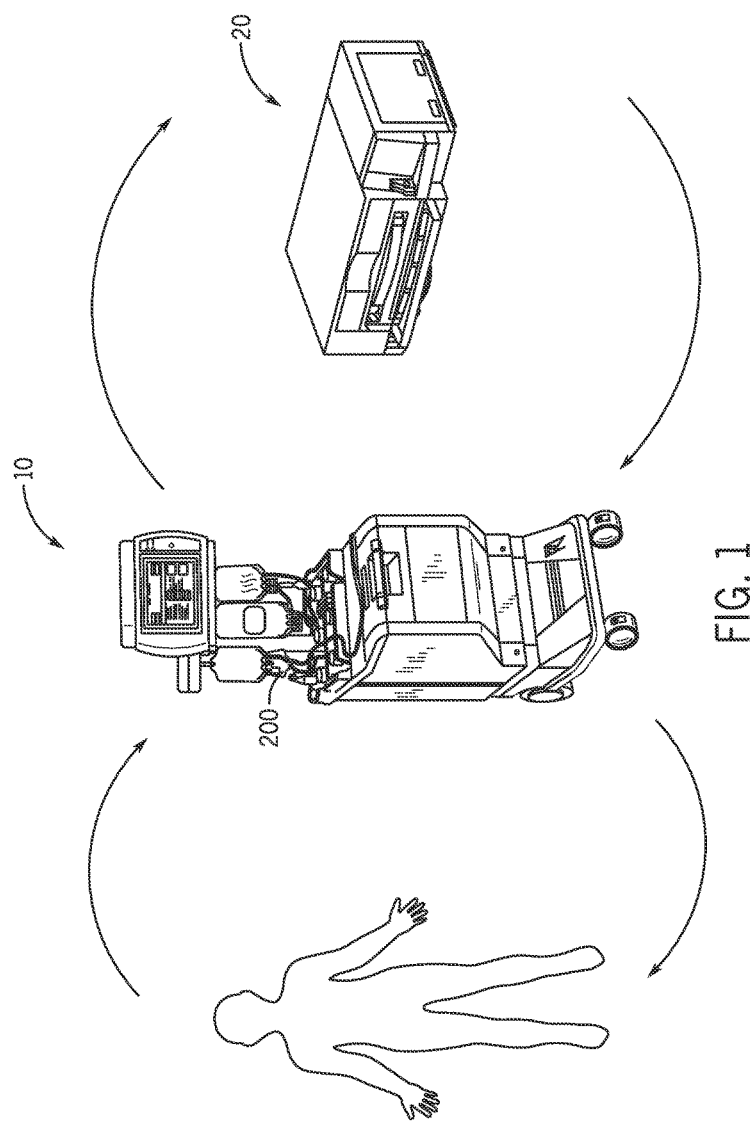
FIG. 1 is an illustration of a patient and first and second medical devices, according to an illustrative embodiment.

Referring now to FIG. 1, one illustrative embodiment will be described with reference to systems and methods for performing extracorporeal photopheresis (ECP) treatment of mononuclear cells utilizing a multifunctional automated apheresis device, a disposable fluid circuit and an independent irradiation device housed separately from the apheresis device. This embodiment comprises a separation component (e.g., apheresis device) 10 and a treatment component (e.g., irradiation device) 20. Irradiation component 20 may be an independent device which is housed separately from and/or spaced apart from separation component 10. Components 10 and 20 may each have a separate power supply and be configured with independent power plugs. Components 10 and 20 may be spaced apart in the vicinity of each other (e.g., on a cart or in the same room) or may be located in separate rooms of a facility. Separation device 10 and irradiation device 20 may be located adjacent to each other. Irradiation device 20 may be on a table top located near or adjacent to separation component 10, allowing an operator or clinician to have access to both devices during a particular treatment procedure. A patient may be connected to a blood processing set, e.g., a fluid circuit 200, which may be a disposable component or may be configured for use with a single patient. Fluid circuit 200 may comprise one or more cassettes, tubes, blood bags, valves, or other components configured to provide a sterile closed pathway between a patient and separation component 10. The system described herein also may include a washing component which may be housed within the separation component 10.

With reference to FIG. 1, whole blood is withdrawn from the patient and introduced into the separation component 10 where the whole blood is separated to provide one or more target cell populations. The target cell population may be mononuclear cells, plasma, red blood cells, platelets, or other components. One or more components separated from the whole blood, such as red blood cells and platelets, may be returned to the patient or collected in pre-attached containers of the blood processing set.

The separated target cell population, e.g., mononuclear cells, is then treated and irradiated in treatment component 20. Treatment of mononuclear cells may comprise the photoactivation of a photoactive agent that has been combined with the mononuclear cells. Once treated, the mononuclear cells may be provided to a washing component, which, as shown in FIG. 1, may be housed within separation component 10. The treated mononuclear cells are separated from a supernatant liquid and the concentrated cells may be returned to the patient. The supernatant liquid will typically include excess and unbound photoactivation agent. The concentrated cells may further be combined with a suitable wash solution within separation/washing component 10. If washing of the treated mononuclear cells is performed, the suspension of mononuclear cells in a wash solution may then be subjected to a centrifugal field (or other environment which can effect separation of the fluid components), whereby the mononuclear cells are concentrated and separated from the supernatant. The supernatant liquid may include any remaining unbound photoactivation agent. Supernatant may then be diverted to an appropriate waste container, while the treated mononuclear cells are returned to the patient, as generally shown in FIG. 1.

Apparatus useful in the collection (and washing) of mononuclear cells include the Amicus® Separator made and sold by Fenwal, Inc., of Lake Zurich, Ill. The apparatus used for the harvesting, collection and reinfusion of mononuclear cells in accordance with the apparatus and methods described herein may be a "multifunctional" automated apheresis device, as is the case with the Amicus® Separator. In other words, the separation component 10 may be a multifunctional automated apparatus that can perform various collection protocols and/or serve multiple purposes, as may be needed by a particular hospital or facility, such that it can be used not only for performing photopheresis treatment of MNC as described herein, but can also be used for other purposes including the collection of blood and blood components including platelets, plasma, red blood cells, granulocytes and/or perform plasma/RBC exchange, among other functions required by the hospital or medical facility.

Apparatus for the irradiation of the mononuclear cells are available from sources such as Cerus Corporation, of Concord, Calif. One example of a suitable irradiation device is described in U.S. Pat. No. 7,433,030, the contents of which is incorporated by reference herein in its entirety. As shown and described in U.S. Pat. No. 7,433,030, an irradiation device preferably includes a tray or other holder for receiving one or more containers during treatment. Other irradiation devices may also be suitable for use with the embodiments described herein, including devices available from Macopharma (e.g., Macogenic, Macogenic G2 devices), Vilber Lourmet, etc.

Effective treatment of the mononuclear cells with light may require that the amount of collected mononuclear cells have a suitable hematocrit. Thus, the mononuclear cells may be diluted with a diluting solution such as plasma or saline. In one example, approximately 15 ml of MNC may be diluted in about 200 ml of plasma.

The diluted mononuclear cells in a container are then combined with the suitable photoactivation agent. Alternatively, the desired volume of the agent may be pre-added to the container. For ECP treatment, the compound 8-methoxypsoralen (8-MOP) has been shown to be an effective photoactivation agent. However, other suitable photoactivation agents may be used, including, for example, a psoralen compound.

Figure 2:
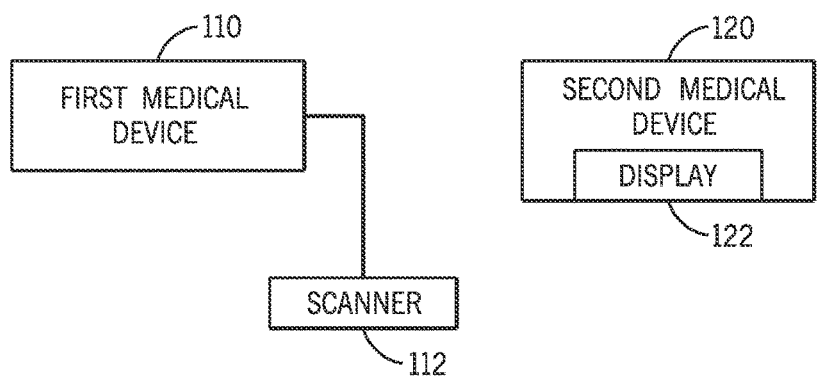
FIG. 2 is a block diagram illustrating components of first and second medical devices, according to an exemplary embodiment.

Referring now to FIG. 2, a first medical device 110 and a second medical device 120 are shown. Each medical device may be configured to perform a different medical operation on a specimen, which may comprise a patient, blood from the patient, or other specimens. Each medical device may comprise a mechanism configured to perform the medical operation. For example, in the case of an apheresis device, the mechanism may comprise a centrifuge and the medical operation may comprise separation of one or more target cell components from the other components. In the case of a blood treatment device, the mechanism may comprise an irradiation device and the medical operation may comprise irradiation of a blood component.

In this embodiment, first medical device 110 may comprise a scanner 112 and second medical device 120 may comprise a display 122. Scanner 112 may comprise any of a variety of scanning technologies configured to scan data from display 122 of second medical device 120. For example, scanner may comprise a bar code reader and display 112 may be configured to display a bar code based on data from a processing circuit of second medical device 120. In other embodiments, scanner may be any other input device which scans an object or machine readable indicator into a computer, such as a digital camera, an image scanner, a 3-D image scanner, a radio frequency ID reader, a biometric reader, etc. Display 112 may be a computer screen such as a liquid crystal display, cathode ray tube, etc. configured to generate or display an indication. The machine readable indicator may comprise a linear barcode, a two-dimensional matrix barcode, an RFID tag, etc.

In one embodiment, a processing circuit of first medical device 110 may be configured to receive scanned data from scanner 112, the input data comprising an indication that a second medical operation was performed by second medical device 120. The processing circuit may be configured to proceed with a first medical operation based on the indication that the second medical operation was performed by the second medical device. For example, upon completion of an irradiation of a blood component by second medical device 120, device 120 displays a 2-dimensional readable construct that is read (e.g., with a barcode scanner) by scanner 112 that is not otherwise in communication (e.g., via a communication network) with second medical device 120. The 2-D readable construct provides an indication that the irradiation has been completed, which may be a step prerequisite to a step to be performed by first medical device 110, such as returning treated blood to a patient. First device 110 may be configured to perform the first medical operation (e.g., returning treated blood to a patient) only if or based on the indication that the treatment step has been completed. The processing circuit of first device 110 may be configured to enable reinfusion of the separated component based on the scanned input data.

As described, in this embodiment the first and second medical devices are not in electronic communication with one another, though in alternative embodiments they devices may be networked. The devices may be independent devices, each having its own housing spaced apart from each other. In this embodiment, an apheresis collection step and an irradiation step may be linked via scanner 112 and display 122 to act as a measure to ensure that irradiation was successfully completed.

In one embodiment, the processing circuit of first device 110 may further be configured to receive a user input signal from a user input device coupled to device 110, after receiving the scanned data, to confirm the user wishes to proceed with the first medical operation. This may come in the form of a prompt to the user provided visually and/or audible, such as, "TREATMENT CONFIRMED, PROCEED WITH REINFUSION?"

The data displayed by display 122 or otherwise provided by device 120 may comprise additional information that is readable as scanned data by scanner 112. For example, the scanned data may further comprise a patient identifier and/or a specimen identifier. The identifier may be scanned by second device 120 using a scanner of its own from a container (e.g., irradiation bag) or other part of an attached disposable kit. Alternatively, a clinician or other operator can input the identifier or other traceability data into second device 120 using a suitable user input device. The processing circuit of device 110 may then be further configured to compare the patient identifier to a patient identifier stored in a memory on the device 110 before proceeding with the first medical operation. For example, data indicating patient "JOHN A. DOE" or patient ID "12345" or even specimen "12345" may be stored in a memory on device 110 and provided by second device 120 to scanner 112 after completion of a treatment step by second device 120. The scanned data may be compared to the stored data to indicate whether treatment of the particular patient or specimen has occurred. If so, first device 110 may be configured to display the patient ID or specimen ID on a display so that a clinician can confirm that the specific specimen has been treated before returning it to the patient. First device 110 may be configured to enable reinfusion of the separated component based on or only if a patient identifier of the input data matches a patient identifier stored in a memory and based on or only if the indication indicates that the separated component has been processed by the blood treatment device.

The data displayed by display 122 or otherwise provided by device 120 may comprise yet further information that is readable as scanned data by scanner 112. Any parameter of the treatment which is recorded by second device 120 may be provided by device 120 to scanner 112, such as UV-A dose delivered, average UV-A intensity, irradiation time, maximum temperature, presence (yes/no) and/or rate of mixing (e.g. agitation), etc. In one example, this data may be displayed on a display of device 120 and read by scanner 112 in the form of a digital camera or other image acquisition device. Scanner 112 may be configured to read the text output on the image, for example using an optical character recognition algorithm or other algorithms, to convert the text to data usable by first device 110. First device 110 may use the data in determining whether to enable or proceed with a medical operation, may use the data in a report to be generated, may transfer the data to a remote server computer for data analysis, or may use the data for other purposes.

In another embodiment, first device 110 may be configured to perform a medical operation on the specimen of the patient (e.g., apheresis) prior to the specimen being manually transferred by a clinician to second device 120. Second device 120 then performs a medical operation (e.g., irradiation) before the specimen is manually transferred back to first device 110 for another medical operation (e.g., reinfusion to the patient).

Figure 3:
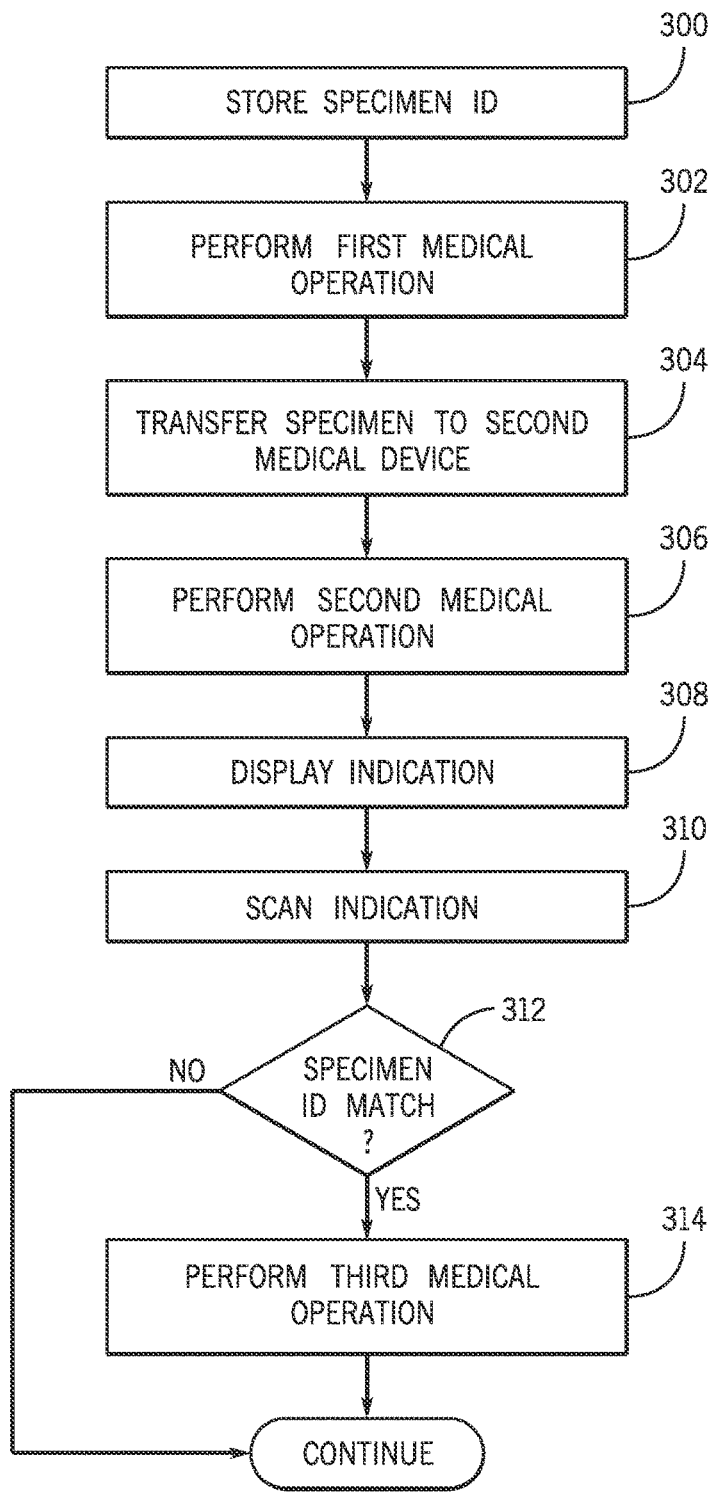
FIG. 3 is a flow chart of a medical procedure having a plurality of operations, according to an exemplary embodiment.

Referring now to FIG. 3, a method of performing a medical operation on a specimen will be described, according to an illustrative embodiment. At a first block 300, a specimen ID is stored. The specimen ID may identify a specimen, such as a target blood component of a human patient's blood. The ID may be or comprise a patient identifier, such as a patient name or numerical or alphanumerical ID. The specimen ID may be stored in a first medical device in a memory. The first medical device may receive the specimen ID via a user input device.

At a block 302, a first medical device is configured to perform a first medical operation on the specimen. In one example, MNCs are collected by the first device. The device may be operated under control of a clinician who loads a container for the MNCs, programs any relevant parameters for the medical operation, and starts the operation. At a block 304, after the collection is complete, a clinician transfers the specimen in its container to a second medical device. The second device may be adjacent the first device or in a different room, floor or other location. In one alternative embodiment, the container may be coupled to both the first and second medical devices so that transfer of the specimen is not needed.

At a block 306, the second medical device is configured to perform a second medical operation on the specimen. In one example, MNCs are irradiated by the second device. The second device may be operated under control of a clinician who loads a container of MNCs, programs any relevant parameters for the irradiation, and starts the operation. At a block 308, the second device displays or otherwise provides a machine readable construct. The construct may comprise one or more of traceability data (e.g., a patient ID, specimen ID, etc.), data indicating the irradiation was successfully completed, data regarding parameters relevant to the irradiation that was conducted, etc.

At a block 310, a scanner scans a machine readable construct from the second medical device, thereby recording the data from the construct in memory on the first medical device. In one example, this block may further comprise operating a character recognition algorithm to generate the indication that the second medical operation has been performed on the specimen. At a block 312, it may be determined whether the specimen ID received via the scanner matches the specimen ID stored in block 300 above. If so, then based on receiving the indication that the second medical operation has been performed, a third medical operation is performed at block 314 using the first medical device.

In other embodiments, additional criteria may be checked before performing the third medical operation. For example, the parameters of the irradiation or other medical procedure performed may be checked against minimum requirements before performing the third operation. As another example, user input to confirm the desire to begin the third medical operation may be received before performing the third operation.

In other embodiments, a report function may be performed using the first medical device based on receiving the indication that the second medical operation has been performed. For example, data indicative of the performance of the second medical operation may be displayed on a display of the first medical device in a report format or in other formats, said data may be printed to a printer, said data may be reported to a networked remote server computer for further data collection, analysis, etc.

According to one embodiment, one or more of the components described herein may be configured to be retrofitted to an existing radiation device. For example, a Macopharma Macogenic or Macogenic G2 device comprises a barcode scanner which may be used to scan a bag/disposable set for traceability information. Additionally, information about UV dose emitted, temperature and duration is reported on the screens of these devices in the form of text and graphs. Post-treatment, the screens could be read directly by scanner 112 of first device 110.

According to another embodiment, the two devices may be in different rooms. For example, an irradiation container comprising the specimen may comprise a read/write tag (e.g., RFID, etc.) and the irradiation device may be configured to record the irradiation information on that tag attached to the specimen, which is then ready by scanner 112 on apheresis device 110.

While described with reference to exemplary medical devices, such as an apheresis device and an irradiation or blood treatment device, the principles described herein may be used with a variety of other medical devices. For example, the principles may be used with any tandem medical and/or lab device procedures. For example, a tandem extracorporeal membrane oxygen (ECMO) and therapeutic plasma exchange (TPE) procedure may use these principles. A tandem plasmapheresis and immunoadsorption or lipid column filtration device may use these principles. An ECMO and continuous renal replacement therapy (CRRT) may use these principles. TPE and CRRT may use these principles. A cell culture and upstream/downstream processing devices (e.g., Xuri Cell Expansion Systems by GE Healthcare and the Lovo cell processor by Fresenius Kabi) may use these principles. In these or other examples, one or more steps of a procedure using the two (or more) devices may be contingent upon the completion of or upon data from a second device before proceeding with an operation or report on the first device. A scanner or other communication method may be used to communicate an indication regarding the treatment (e.g., treatment completed, patient and/or specimen ID, treatment parameters, etc.) from one such medical device to another.

As mentioned, a tandem plasmapheresis and immunoadsorption or lipid column filtration device may use these principles. The first device may comprise the plasmapheresis machine and the second device may comprise an immunoadorption device, such as, for example, the ADAsorb device sold by Medicap Clinic, Gmbh, Ulrichstein, Germany. In a first step, an adsorber type suitable for the patient is selected. Blood is drawn from the patient, mixed with appropriate anticoagulants, and separated into cells and plasma by a filtrative or centrifugal blood cell separator device. Next, a predefined volume of plasma is directed to a first column having a first adsorber, followed by loading of a second adsorber into a second column. While loading the second adsorber, the first adsorber may be regenerated at the same time with certain solutions. The treatment may be a continuous procedure by which the adsorbers are loaded and regenerated as often as needed. Finally, upon confirmation of a complete immunoadsorption, using the scanner as described herein, the first device is configured to return the cleansed plasma to the patient continuously as whole blood along with other cellular components.

In some embodiments, the interaction of the first and second devices (or more) may proceed in a "batch" like manner, in which the first device performs an operation, then the second device performs an operation and optionally, the first device performs another operation. In alternative embodiments, the first and second (or more) devices may operate in a continuous manner. For example, if the first device is a plasmapheresis device, the plasmapheresis device may be configured to continuously generate plasma which is fed to a second device for filtration and post filtration, after which the plasma is fed back to the first device for reinfusion, all in a continuous manner. The scanner of the first device may be configured to read indications from the second device continuously, intermittently, or otherwise periodically to confirm that the second device processing is proceeding, complete, and/or otherwise proper. If the scanner receives an indication that the second device is not complete or otherwise proceeding as planned, the first device may pause reinfusion until further operator input is provided.

Each medical device may comprise a processing circuit comprising analog and/or digital circuit components configured to perform the medical operations and functions thereof discussed herein. The components may comprise one or more of a microprocessor, microcontroller, application-specific integrated circuit, discrete circuit components, digital memory (e.g., read-only memory, flash memory, programmable ROM, random access memory, etc.) programmed with one or more algorithms to carry out medical operations. The algorithms may be carried out using various types of digital electronic circuitry, or in computer software, hardware or firmware, including the structures disclosed in this specification and their structural equivalents, or in combinations of one or more of them.

The programmed circuits may comprise a computer storage medium which is tangible and non-transitory, but not a propagated signal.

In some implementations, the medical devices may each include a communications circuit, such as a networking adapter. The communications circuit may be configured to enable communications with a computing or communications network and/or other computing systems. In various illustrative implementations, any type of networking configuration may be achieved using the communications circuit, such as wired (e.g., via Ethernet), wireless (e.g., via Wi-Fi, Bluetooth, etc.), pre-configured, ad-hoc, LAN, WAN, etc.

To provide for interaction with a user, the subject matter described in this specification can be carried out using a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous

The invention claimed is:

1. A method of performing a medical operation on a specimen, comprising:
   performing a first medical operation on the specimen using a first medical device;
   scanning a two-dimensional machine readable construct from a computer screen of a second medical device;
   receiving an indication from the machine readable construct that a second medical operation has been performed on the specimen by the second medical device;
   based on receiving the indication that the second medical operation has been performed, performing at least one of a third medical operation using the first medical device and a report function using the first medical device.

2. The method of claim 1, wherein the scanning is performed using a digital camera, further comprising operating a character recognition algorithm to generate the indication that the second medical operation has been performed on the specimen.

3. The method of claim 2, wherein the character recognition algorithm further generates a specimen identifier.

4. The method of claim 3, wherein the specimen identifier comprises a patient identifier.

5. The method of claim 3, wherein the character recognition algorithm further generates at least two parameters representative of the second medical operation performed by the second medical device.

6. A method of operating an apheresis device, comprising:
separating a component from a patient's blood at the apheresis device;
scanning a machine readable indicator from a computer screen of a blood treatment device separate from the apheresis device, the indicator indicating that the separated component has been processed by the blood treatment device;
receiving input data from the scanner; and
enabling reinfusion of the separated component to the patient based on the input data.

7. The method of claim 6, wherein the machine readable indicator is a linear barcode or a two-dimensional matrix barcode.

8. The method of claim 6, wherein the input data further comprises a patient identifier which identifies the patient.

9. The method of claim 6, further comprising receiving a user input signal from a keyboard, after receiving the input, to confirm the user wishes to proceed with the first medical operation.

10. The method of claim 6, further comprising receiving a patient identifier, determining whether the patient identifier matches a patient identifier stored in memory, determining from the input data whether the separated component has been processed by the blood treatment device, and enabling the reinfusion based on the patient identifiers matching and the input data indicating the separated component has been processed.

11. The method of claim 6, further comprising processing the separated component by irradiating the separated component at the blood treatment device separate from the apheresis device.

12. The method of claim 11, wherein the apheresis device and the blood treatment device are not in electronic communication with each other.

13. The method of claim 6, wherein the separated component is plasma, further comprising processing the plasma by immunoadsorption or lipid column filtration.

14. A method, comprising:
providing a first medical device;
performing a second medical operation using a second medical device which is separate from the first medical device and comprises a computer screen;
displaying data on the computer screen;
scanning the data on the computer screen, the scanned data comprising an indication that the second medical operation was performed by the second medical device;
receiving the scanned data at the first medical device;
determining at the first medical device that the second medical operation was performed; and
based on the determination that the second medical operation was performed, proceeding with a first medical operation using the first medical device.

15. The method of claim 14, wherein the first medical device and the second medical device are not in electronic communication with one another.

16. The method of claim 15, wherein the first medical device and the second medical device are independent devices, each having its own housing spaced apart from each other.

17. The method of claim 16, wherein the scanned data comprises a patient identifier, further comprising comparing the patient identifier to a patient identifier stored in a memory of the first medical device before proceeding with the first medical operation.

18. The method of claim 17, further comprising performing a third medical operation for the patient at the first medical device prior to receiving the scanned data from the scanner, wherein the first medical operation, second medical operation and third medical operation are performed with respect to the same patient.

19. The method of claim 18, further comprising:
after receiving the scanned data, displaying a text prompt on a screen of the first medical device to request whether a user wishes to proceed with the first medical operation;
receiving a user input signal after receiving the scanned data to confirm the user wishes to proceed with the first medical operation, wherein the user input signal is received via a user pressing the user input device.

20. The method of claim 18, wherein performing the second medical operation comprises irradiation of a blood component of a patient, wherein performing the first medical operation comprises returning the blood component to the patient, wherein performing the third medical operation comprises separating the blood component from blood of the patient.

* * * * *